US00PP29426P3

(12) United States Plant Patent
MacGregor et al.

(10) Patent No.: US PP29,426 P3
(45) Date of Patent: Jun. 26, 2018

(54) *ANEMONE* PLANT NAMED 'MACANE005'

(50) Latin Name: *Anemone hupehensis* Lemoine x *A. rupicola* Cambess
Varietal Denomination: Macane005

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 108 days.

(21) Appl. No.: 15/330,067

(22) Filed: Aug. 1, 2016

(65) Prior Publication Data

US 2018/0035591 P1 Feb. 1, 2018

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/025; A01H 5/02; A01H 5/00
See application file for complete search history.

(56) References Cited

U.S. PATENT DOCUMENTS

PP23,132 P2 * 10/2012 MacGregor ..... A01H 5/025
Plt./263.1

OTHER PUBLICATIONS

A. Verschoor Perennials Assortment—list bare root Perennials Autumn 2015—Spring 2016, retrieved on Dec. 13, 2017 retrieved from the Internet at http://www.verschoorperennials.com/documenten/catalogue/Assortment-list%202015-2016.pdf, pp. 1, 3, 57. (Year: 2015).*
Shoot Gardening *Anemone* 'Elfin Swan', retrieved on Dec. 13, 2017, retrieved from the Internet at https://www.shootgardening.co.uk/plant/anemone-elfin-swan, 3 pp. (Year: 2017).*
Upov Pluto Plant Variety Database Dec. 12, 2017, retrieved on Dec. 12, 2017, retrieved from the Internet at https://www3.wipo.int/pluto/user/en/index.jsp, 1 page. (Year: 2017).*

* cited by examiner

*Primary Examiner* — June Hwu
(74) *Attorney, Agent, or Firm* — Samuel R. McCoy, Jr.

(57) ABSTRACT

'Macane005' is a new and distinctive variety of *Anemone hupehensis* Lemoine × *A. rupicola* Cambess plant which is characterized by a compact growth habit, white flowers with the tepals alternating between dark pink and white on the lower surface semi-double flowers, and early flowering. The new variety propagates successfully by stem cuttings and tissue culture and has shown to be uniform and stable in the resulting generations from asexual propagation.

3 Drawing Sheets

Latin name of the genus and species: The Latin name of the genus and species of the novel variety disclosed herein is *Anemone hupehensis* Lemoine × *A. rupicola* Cambess.

Variety denomination: The inventive variety of *Anemone* disclosed herein has been given the variety denomination 'Macane005'.

BACKGROUND OF THE INVENTION

The present invention relates to a new and distinct cultivar of *Anemone*, which has been given the variety denomination of 'Macane005'. Its market class is PLT/263.1.

Parentage: 'Macane005' is the result of a controlled cross-pollination breeding program carried out by the inventors at their commercial nursery in Kirkcudbright, Scotland, in 2007. The inventors performed a controlled cross-pollination of the emasculated mother plant, an unnamed *Anemone hupehensis* Lemoine × *A. rupicola* Cambess seedling developed by the inventors (unpatented), with the pollen parent, an unnamed dwarf double pink *Anemone hupehensis* seedling, also developed by the inventors (unpatented). Said pollination was performed in an insect proof environment. Seed from said cross was harvested, then germinated, and the resulting seedlings were then grown to a mature size in a protected poly tunnel greenhouse. In July of 2008, the inventors selected the new *Anemone* cultivar due to its unique flower and bloom characteristics. This new and distinctive cultivar was given the name 'Macane005'.

Asexual Reproduction: Asexual reproduction of 'Macane005' was first accomplished in 2008 by way of root cuttings at the inventor's nursery in Kirkcudbright, Scotland. After several years of experimentation, 'Macane005' was also asexually reproduced by way of meristematic tissue culture micro propagation at a plant tissue culture laboratory in the Netherlands. Successive generations produced from both root cuttings and tissue culture have shown that the unique features of the instant cultivar are stable and reproduce true to type.

SUMMARY OF THE INVENTION

The cultivar 'Macane005' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anemone* cultivar, 'Macane005'. These traits, in combination, distinguish 'Macane005' as a new and distinct cultivar.

1. *Anemone* 'Macane005' exhibits a compact growth habit; and
2. *Anemone* 'Macane005' exhibits white flowers with the lower surface of the tepals appearing to alternate between dark pink and white; and
3. *Anemone* 'Macane005' exhibits semi-double flowers; and
4. *Anemone* 'Macane005' exhibits early flowering, from mid-June until autumn when grown in Kirkcudbright, Scotland.

BOTANICAL DESCRIPTION OF THE PLANT

Figure 1:
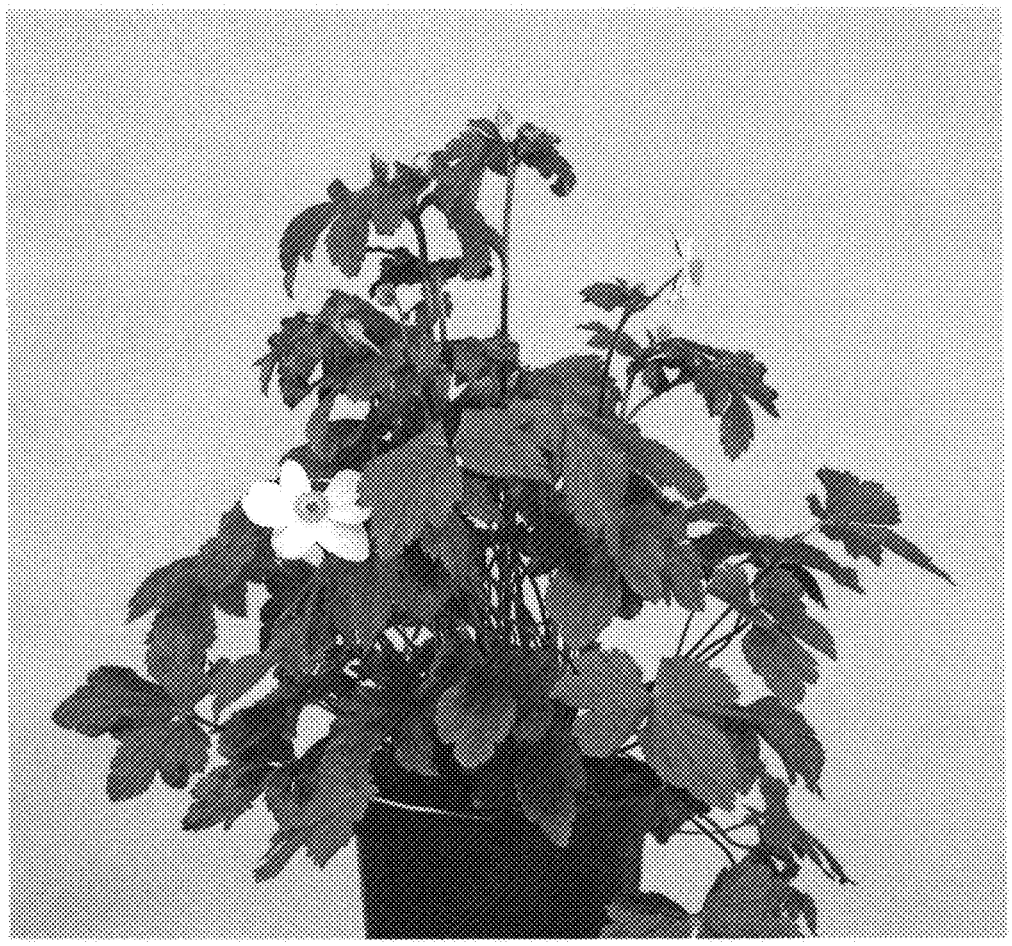
FIG. 1 shows, as nearly true as it is reasonably possible to make the same in color illustrations of this type, the typical foliage and growth characteristics of the new cultivar, 'Macane005'. The plant shown is approximately one year old, potted into a 3 liter nursery pot, grown outdoors in Kirkcudbright, Scotland at a commercial nursery.
Figure 2:
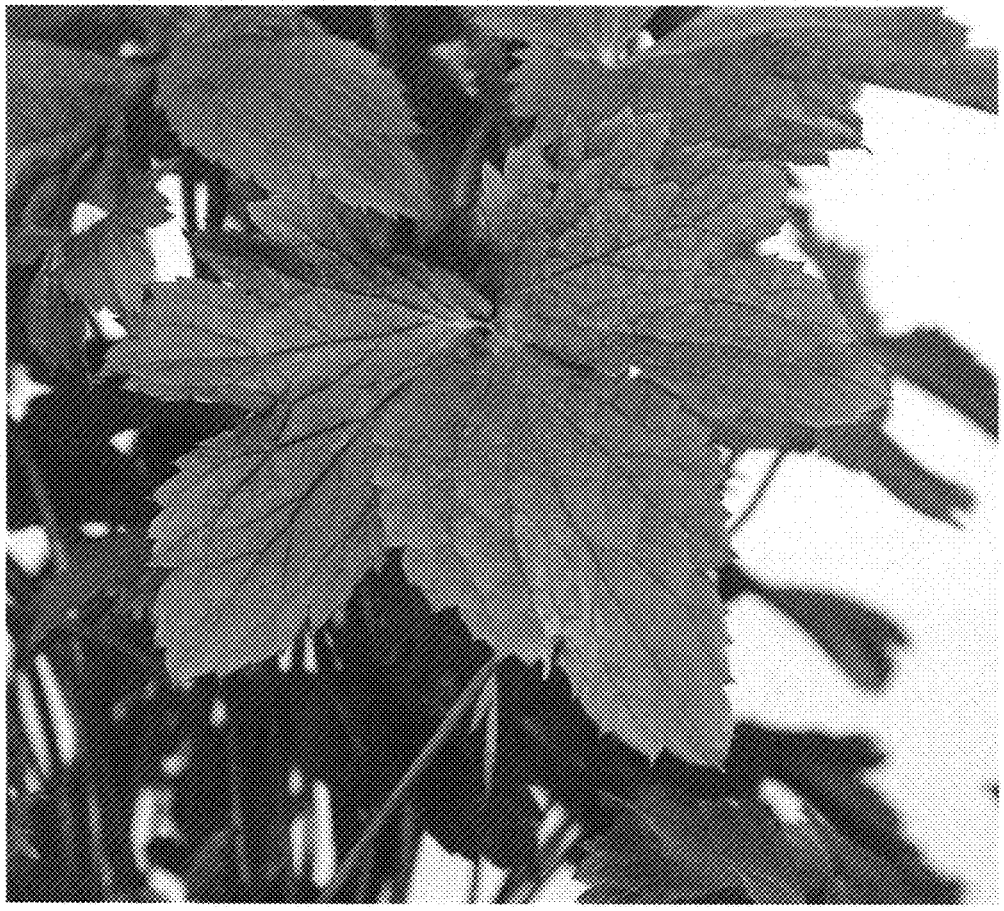
FIG. 2 shows, as nearly true as it is reasonably possible to make the same in color illustrations of this type, the typical foliage of the plant in FIG. 1.
Figure 3:
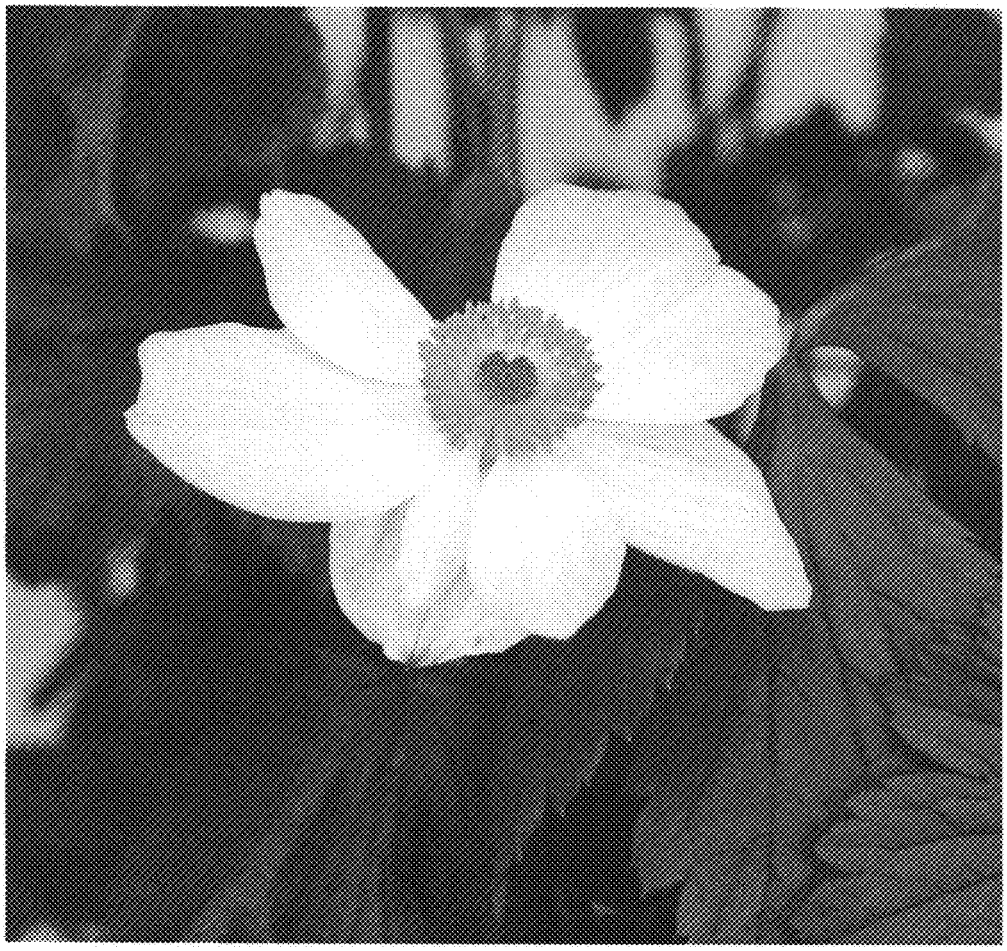
FIG. 3 shows, as nearly true as it is reasonably possible to make the same in color illustrations of this type, the typical flower of the plant in FIG. 1.

The following is a detailed botanical description of a new and distinct variety of *Anemone hupehensis* Lemoine × *A. rupicola* Cambess known as 'Macane005', based upon observations of one year old plants, potted into 3 liter nursery pots and grown outdoors at a commercial nursery in Kirkcudbright, Scotland. Plants were grown in full sun to partial shade using accepted fertility and irrigation practices for *Anemone* plants. With the exception of nematicides, no chemical pest control measures were employed. Furthermore, no artificial light or photoperiodic treatments were given to the plants. Observation data was recorded in June of 2016.

Those skilled in the art will appreciate that certain characteristics will vary with older or, conversely, with younger plants. 'Macane005' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition, 2015.

A botanical description of 'Macane005' and comparisons with the parents and most similar variety of common knowledge are provided below.

General plant description:

*Growth rate*.—Moderate.

*Plant vigor*.—Moderate.

*Growth habit*.—Herbaceous perennial; globular plant habit with leaves developing from basal rosettes; flowering stems arising from the rosette also bear foliage; no lateral branching is present.

*Height*.—29.9 cm to the top of the foliar plane; 39.7 to the top of the floral plane.

*Width*.—52.3 cm.

*Propagation*.—Root cuttings and tissue culture.

*Time to produce flowering plant from rooted cutting*.—Approximately 6 to 8 weeks to produce a rooted young plant; 16 to 20 months to produce a marketable potted plant.

*Pest resistance and susceptibility*.—Similar to other *Anemone* varieties.

*Environmental tolerances*.—Adapt to, at least, USDA Zones 4 to 9 and temperatures ranging from minus 30 degrees Celsius to 35 degrees Celsius; moderate tolerance to rain; moderate tolerance to wind.

Root system:

*Type*.—Moderately fibrous root system.

*Diameter*.—Largest roots measuring 2 mm in diameter.

*Texture*.—Smooth; lacking root hairs.

*Color*.—Brown, RHS 200B to 200C.

*Branching*.—Freely branched.

*Density*.—Moderately dense.

*Distribution*.—Roots distributed evenly throughout the soil profile, from shallow to deep.

Foliage:

*Arrangement*.—Leaves alternating in a basal rosette.

*Type*.—Simple.

*Quantity*.—Approximately 4 leaves per basal rosette.

*Attachment*.—Petiolate.

*Dimensions*.—12.8 cm long, excluding the petiole, and 12.5 cm wide.

*Leaf attitude*.—Leaves in an average angle of 45° to soil level.

*Leaf shape*.—Broad ovate to near orbiculate; three lobed.

*Leaf apex*.—Acute to very short apiculate.

*Leaf base*.—Hastate; lobes free to slightly overlapping.

*Lobes*.—Leaves with three lobes; lobes cleft to deeply cleft; sinus depth is medium to deep.

*Leaf margin*.—Serrate.

*Texture and luster, adaxial surface*.—Smooth and slightly glossy.

*Texture and luster, abaxial surface*.—Smooth and moderately glossy.

*Pubescence, adaxial surface*.—Glabrous.

*Pubescence, abaxial surface*.—Sparsely covered with short soft hairs with an average length of 1.0 mm; colored near RHS NN155D.

*Color*.—Juvenile foliage color, adaxial surface — Green; RHS 141A to 141B. Juvenile foliage color, abaxial surface — Green, RHS 138A, to yellow-green, RHS 147B. Mature leaf color, adaxial surface — Green, RHS NN137B. Mature leaf color, abaxial surface — Yellow-green, RHS 147B.

*Venation*.—Pattern — Laciniate. Vein color, adaxial surface — Yellow-green, RHS 144B. Vein color, abaxial surface — Yellow-green, RHS 146B.

*Petiole*.—Length — Average of 226 mm. Diameter — Average of 2.5 mm. Color, adaxial surface — Yellow-green, RHS 146B, and tinged brown, RHS 200B; greyed-purple towards the base, near RHS 187A. Color, abaxial surface — Yellow-green, RHS 146B to 146C; greyed-purple towards the base, near RHS 187A. Texture — Very sparsely covered with short soft hairs; average length of hairs is 1.0 mm;

colored white, RHS NN155D. Luster, adaxial and abaxial surfaces — Glossy.

*Stipule*.—None.

Inflorescence:

*Habit*.—Cyme.

*Natural flowering season*.—Late spring into summer in Kirkcudbright, Scotland.

*Time to flower or response time*.—Approximately 10 months.

*Height*.—6.0 cm high, from the lowest branching of the peduncle to the apex of the inflorescence.

*Diameter*.—8.0 cm.

*Quantity of flowers per inflorescence*.—3, on average.

*Quantity of flowers per plant*.—3, on average.

*Quantity of flower buds per plant*.—30, on average.

*Quantity of flowers and flower buds per plant*.—33, on average.

*Peduncles*.—Length — Average of 314 mm. Diameter — Average of 3.5 mm. Angle — Average angle to soil level is approximately 80 degrees. Strength — Strong. Texture — Smooth. Pubescence — Very sparsely covered with soft hairs; average length of hairs is 0.75 mm; hairs translucent and colored greyed-white, RHS 156D. Luster — Slightly glossy. Color — Yellow-green, RHS 144B; moderately to strongly tinged greyed-purple, RHS N186C.

*Pedicels*.—Length — Average of 38 mm. Diameter — Average of 2 mm. Angle — Average angle to peduncle axis is approximately 45 degrees. Strength — Moderately strong. Texture — Densely covered with short soft hairs; average length of hairs is 1.0 mm; colored greyed-white, RHS 156C to 156D. Luster — Slightly glossy. Color — Greyed-brown, RHS N199A; proximal and distal end is yellow-green, RHS 148A and 148B.

Bud:

*Shape*.—Ovate.

*Length*.—Average of 15 mm.

*Diameter*.—Average of 10 mm.

*Color*.—Greyed-purple, RHS 183D; underside is tinged yellow-green, RHS 149B.

*Texture*.—Smooth.

*Pubescence*.—Dense wooly pubescence; average length of hairs is 1 mm; color of hairs is greyed-white, RHS 156D.

*Luster*.—Matte.

Flower:

*Type and form*.—Rotate; semi-double.

*Aspect*.—Outwardly to upright.

*Flowering habit*.—Moderately freely flowering.

*Flower longevity on plant*.—Approximately 10 days.

*Persistent or self-cleaning*.—Self-cleaning.

*Fragrance*.—Non-fragrant.

*Diameter*.—Average of 73 mm.

*Depth*.—Average of 32 mm.

*Tepals*.—Quantity — 8. Arrangement — Rotate; the unfused tepals arranged in 2 whorls. Length — 35 mm, on average; varying between 30 to 39 mm. Width — 26 mm, on average; varying between 15 to 35 mm. Shape — Ovate to obovate. Apex — Obtuse. Base — Cuneate. Margin — Entire; not undulated. Texture, luster and pubescence of the upper surface — Upper surface glabrous, slightly glossy, and moderately velvety. Texture, luster and pubescence of the lower surface — Smooth, matte, and densely covered with appressed soft, silky hairs; average length of hairs is 0.75 mm; colored greyed-white, RHS 156D. Color — When opening, upper surface — White, RHS NN155A, and occasionally tinged purple, RHS 76B to 76C. When opening, lower surface — A combination of white, RHS NN155A, and red-purple, RHS 71B and 71C. Fully opened, upper surface — White, RHS NN155A, and occasionally tinged purple, RHS 76C. Not fading. Fully opened, lower surface — A combination of white RHS NN155A, and red-purple, RHS 72B. Not fading. Tepal venation — Fully opened, upper surface — White, RHS NN155A, and occasionally tinged purple, RHS 76C. Fully opened, lower surface — A combination of white, RHS NN155A, and red-purple, RHS 72B.

Reproductive organs:

*Stamens*.—Quantity — 300, on average. Anthers — Shape — Oblong. Length — Approximately 0.1 mm. Width — Approximately 0.75 mm. Color — Yellow-orange, RHS 14A. Filaments — Length — 8 mm, on average. Color — Yellow, RHS 3C. Pollen — Color — Yellow, RHS 11D. Quantity — Low.

*Pistil*.—Quantity — 160, on average. Length — 1.0 mm. Style — Length — 0.5 mm. Color — Green, RHS 143C. Stigma — Shape — Club-shaped. Dimensions — 0.5 mm long and 0.5 cm in diameter. Color — Greyed-purple, RHS 183A. Ovary Color — Yellow-green, RHS 144A.

Seed and fruit: No fruit or seeds have been detected to date.

COMPARISONS WITH THE PARENT PLANTS

Plants of the new cultivar 'Macane005' may be distinguished from its seed parent, an unnamed *Anemone* seedling, by the characteristics described in Chart 1.

CHART 1

| Characteristic | 'Macane005' | Unnamed seed parent |
|---|---|---|
| Plant height. | 50 cm. | 70 cm. |
| Flower color. | White with white and dark pink reverse. | White with blue reverse. |

Plants of the new cultivar 'Macane005' differ from the pollen parent, an unnamed *Anemone* seedling, by the characteristics described in Chart 2.

CHART 2

| Characteristic | 'Macane005' | Unnamed pollen parent |
|---|---|---|
| Plant height | 50 cm. | 40 cm. |
| Flowering season. | Mid-June to September in Kirkcudbright, Scotland. | August to October in Kirkcudbright, Scotland. |
| Flower habit; petal count. | Semi-double. | Double. |
| Flower color. | White with white and dark pink reverse. | Dark pink. |

COMPARISONS WITH THE MOST SIMILAR VARIETY OF COMMON KNOWLEDGE

Plants of the new cultivar 'Macane005' are most similar to the commercial variety, *Anemone* 'Macane001' (U.S.

Plant Pat. No. 23,132). A comparison of 'Macane005' with *Anemone* 'Macane001' is described in Chart 3.

CHART 3

| Characteristic | 'Macane005' | 'Macane001' |
|---|---|---|
| Plant height. | 50 cm. | 60 cm. |
| Flowering season. | Mid-June to September in Kirkcudbright, Scotland. | April to September in Kirkcudbright, Scotland. |
| Flower habit; petal count. | Semi-double. | Single. |

CHART 3-continued

| Characteristic | 'Macane005' | 'Macane001' |
|---|---|---|
| Flower color. | White with white and dark pink reverse. | White with blue reverse. |

That which is claimed is:

1. A new and distinct variety of *Anemone* plant named 'Macane005', substantially as described and illustrated herein.

* * * * *